US009949720B2

(12) United States Patent
Southard et al.

(10) Patent No.: US 9,949,720 B2
(45) Date of Patent: Apr. 24, 2018

(54) SYSTEMS AND METHODS FOR ULTRASOUND-BASED MEDICAL DEVICE ASSESSMENT

(71) Applicant: C. R. Bard, Inc., Murray Hill, NJ (US)

(72) Inventors: Jeanette E. Southard, Park City, UT (US); Jeremy B. Cox, Salt Lake City, UT (US); Paul D. Morgan, Draper, UT (US); Shayne Messerly, Kaysville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1017 days.

(21) Appl. No.: 13/656,563

(22) Filed: Oct. 19, 2012

(65) Prior Publication Data
US 2013/0102889 A1 Apr. 25, 2013

Related U.S. Application Data

(60) Provisional application No. 61/550,332, filed on Oct. 21, 2011.

(51) Int. Cl.
A61B 17/34 (2006.01)
A61B 8/00 (2006.01)
(Continued)

(52) U.S. Cl.
CPC .......... A61B 8/4427 (2013.01); A61B 8/0841 (2013.01); A61B 8/4455 (2013.01);
(Continued)

(58) Field of Classification Search
CPC .... A61B 8/00; A61B 8/12; A61B 8/42; A61B 8/46; A61B 8/4209; A61B 8/4245;
(Continued)

(56) References Cited

U.S. PATENT DOCUMENTS 5,325,293 A 6/1994 Dorne
5,549,554 A 8/1996 Miraki
(Continued)

FOREIGN PATENT DOCUMENTS

WO 2013059714 A1 4/2013

OTHER PUBLICATIONS

PCT/US12/61182 International Seach Report and Written Opinion dated Mar. 11, 2013.

Primary Examiner — Tse Chen
Assistant Examiner — Nate S Sunwoo
(74) Attorney, Agent, or Firm — Rutan & Tucker, LLP

(57) ABSTRACT

Systems and methods for assisting the placement of a catheter within the body of a patient through the use of an ultrasound imaging system are disclosed. In particular, the systems and methods described herein enable a clinician to determine, prior to insertion of the medical device, how much of the device will be disposed within the vessel, thus enabling the clinician to choose a catheter with suitable length. In one embodiment, an ultrasound imaging system for assisting with placement of the medical device comprises a console, a probe for producing an image of a target location, and a processor. The processor provides to a user proximity information relating to the anticipated proximity of the medical device to the target location prior to insertion of the medical device. A display is included for depicting the image, target location depth, and the proximity information of the medical device to the target location.

30 Claims, 18 Drawing Sheets

(51) Int. Cl.
  *A61B 8/08* (2006.01)
  *A61B 34/00* (2016.01)
(52) U.S. Cl.
  CPC ............ *A61B 34/25* (2016.02); *A61B 8/0891* (2013.01); *A61B 8/465* (2013.01); *A61B 2017/3413* (2013.01)
(58) Field of Classification Search
  CPC ................ A61B 8/4254; A61B 8/4263; A61B 2017/3417; A61B 2017/34; A61B 2017/3403
  USPC ........ 600/424, 433, 434, 435, 464, 466, 467
  See application file for complete search history.

(56) References Cited

U.S. PATENT DOCUMENTS

| | | | |
|---|---|---|---|
| 5,573,529 A | 11/1996 | Haak et al. | |
| 5,908,387 A | 6/1999 | LeFree et al. | |
| 5,970,119 A | 10/1999 | Hofmann | |
| 6,074,367 A | 6/2000 | Hubbell | |
| 6,543,642 B1 | 4/2003 | Milliorn | |
| 6,592,565 B2 | 7/2003 | Twardowski | |
| 6,601,705 B2 | 8/2003 | Molina et al. | |
| 6,613,002 B1 | 9/2003 | Clark et al. | |
| 6,687,386 B1 | 2/2004 | Ito et al. | |
| 6,754,608 B2 | 6/2004 | Svanerudh et al. | |
| 6,840,379 B2 | 1/2005 | Franks-Farah et al. | |
| 6,857,196 B2 | 2/2005 | Dalrymple | |
| 7,831,449 B2 | 11/2010 | Ying et al. | |
| 2003/0047126 A1 | 3/2003 | Tomaschko | |
| 2003/0106825 A1 | 6/2003 | Molina et al. | |
| 2004/0055925 A1 | 3/2004 | Franks-Farah et al. | |
| 2005/0000975 A1 | 1/2005 | Carco et al. | |
| 2006/0015039 A1 | 1/2006 | Cassidy et al. | |
| 2007/0043341 A1* | 2/2007 | Anderson et al. | 606/12 |
| 2007/0073155 A1* | 3/2007 | Park et al. | 600/461 |
| 2007/0199848 A1 | 8/2007 | Ellswood et al. | |
| 2008/0033293 A1* | 2/2008 | Beasley et al. | 600/437 |
| 2008/0033759 A1 | 2/2008 | Finlay | |
| 2008/0051657 A1* | 2/2008 | Rold | 600/440 |
| 2008/0177186 A1 | 7/2008 | Slater et al. | |
| 2008/0300491 A1* | 12/2008 | Bonde et al. | 600/461 |
| 2009/0143672 A1 | 6/2009 | Harms et al. | |
| 2009/0143684 A1 | 6/2009 | Cermak et al. | |
| 2009/0156926 A1 | 6/2009 | Messerly et al. | |
| 2010/0211026 A2* | 8/2010 | Sheetz et al. | 604/288.02 |
| 2010/0312121 A1 | 12/2010 | Guan | |
| 2011/0071404 A1* | 3/2011 | Schmitt et al. | 600/479 |

* cited by examiner

|  | Catheter Length selected {142} | | | | | {140} |
| --- | --- | --- | --- | --- | --- | --- |
|  | 1.00" | 1.16" | 1.25" | 1.75" | 1.88" | 2.00" |
|  | Length in vessel displayed | | | | | |
| Needle Guide Depth (cm) | (in) | (in) | (in) {146} | (in) | (in) | (in) |
| 0.25 | 0.71 | 0.87 | 0.96 | 1.46 | 1.59 | 1.71 |
| 0.50 | 0.59 | 0.75 | 0.84 | 1.34 | 1.47 | 1.59 |
| 0.75 | 0.51 | 0.67 | 0.76 | 1.26 | 1.39 | 1.51 |
| 1.00 | - | 0.55 | 0.64 | 1.14 | 1.27 | 1.39 |
| 1.25 | - | - | 0.52 | 1.02 | 1.15 | 1.27 |
| 1.50 | - | - | - | 0.91 | 1.04 | 1.16 |

PIV
- yellow ○ 24G
- blue ○ 22G
- pink ○ 20G
- green ○ 18G
- gray ○ 16G

190

Dialysis
- orange ○ 17G
- green ○ 16G
- ivory ○ 15G
- pink ○ 14G

192

Blood Draw
- royal blue ○ 25G
- lt blue ○ 23G
- black ○ 22G
- green ○ 21G
- yellow ○ 20G
- cream ○ 19G

194

IDC
- pink ○ 20G
- green ○ 18G

196

*FIG. 11*

SYSTEMS AND METHODS FOR ULTRASOUND-BASED MEDICAL DEVICE ASSESSMENT

CROSS-REFERENCE TO RELATED APPLICATIONS

This application claims the benefit of U.S. Provisional Patent Application No. 61/550,332, filed Oct. 21, 2011, and titled "System and Method for Ultrasound-Based Medical Device Assessment," which is incorporated herein by reference in its entirety.

BRIEF SUMMARY

Briefly summarized, embodiments of the present invention are directed to systems and methods for assisting the placement of a medical device, such as a catheter, within a vessel or other suitable location within the body of a patient through the use of an ultrasound imaging system. In particular, the systems and methods described herein enable a clinician to determine, prior to insertion of the medical device, how much of the device will be disposed within the vessel, thus enabling the clinician to choose a catheter with suitable length so as to ensure a sufficient portion of the catheter is disposed within the vessel.

In one embodiment, an ultrasound imaging system for assisting with placement of a medical device near a target location within a body of a patient is disclosed. The system comprises a console, a probe including a needle guide that produces an ultrasound image of the target location, and a processor. The processor provides to a user proximity information relating to the anticipated proximity of the medical device to the target location prior to insertion of the medical device into the body. A display is also included for depicting the ultrasound image, depth information of the target location, and the proximity information of the medical device with respect to the target location. In one embodiment, the medical device is a catheter. In this case, the proximity information relates to the amount of a distal portion of the catheter that would be disposed within the vessel when the catheter is inserted into the body. In another embodiment, the proximity information relates to whether an access needle that is to be inserted into the body to access an implanted access port is sufficiently long as to adequately access a fluid reservoir of the port.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 8 is a lookup table used by the system of FIG. 1 according to one embodiment;

FIG. 11 shows various gauge sizes for medical devices for use with the system of FIG. 1;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to methods for assisting the placement of an elongate medical device, such as a catheter, within a vessel or other suitable location within the body of a patient through the use of an ultrasound imaging system. In particular, the systems and methods described herein enable a clinician to determine, prior to insertion of the medical device, how much of the device will be disposed within the vessel, thus enabling the clinician to choose a catheter with suitable length so as to ensure a sufficient portion of the catheter is disposed within the vessel.

In another embodiment, color-coded icons, each representing a cross sectional size of a corresponding catheter or other suitable device, are depicted on a display of the ultrasound imaging system, together with and in relation to an ultrasound image of the vessel to be accessed. The color-coding of the catheter icons enables the clinician to readily identify which size of catheter will be most suitable for insertion into the imaged vessel.

In addition, in one embodiment, the color-coded icons are scalable in size according to scale of the accompanying ultrasound image so as to preserve a 1:1 relationship in size. As such, the clinician is able to discern the cross sectional size of one or more catheters represented by their corresponding icons in scalar relation to the cross sectional image of the vessel depicted on the display of the ultrasound imaging system, and thus choose a catheter of suitable gauge for subsequent insertion into the ultrasonically imaged vessel.

Figure 1:
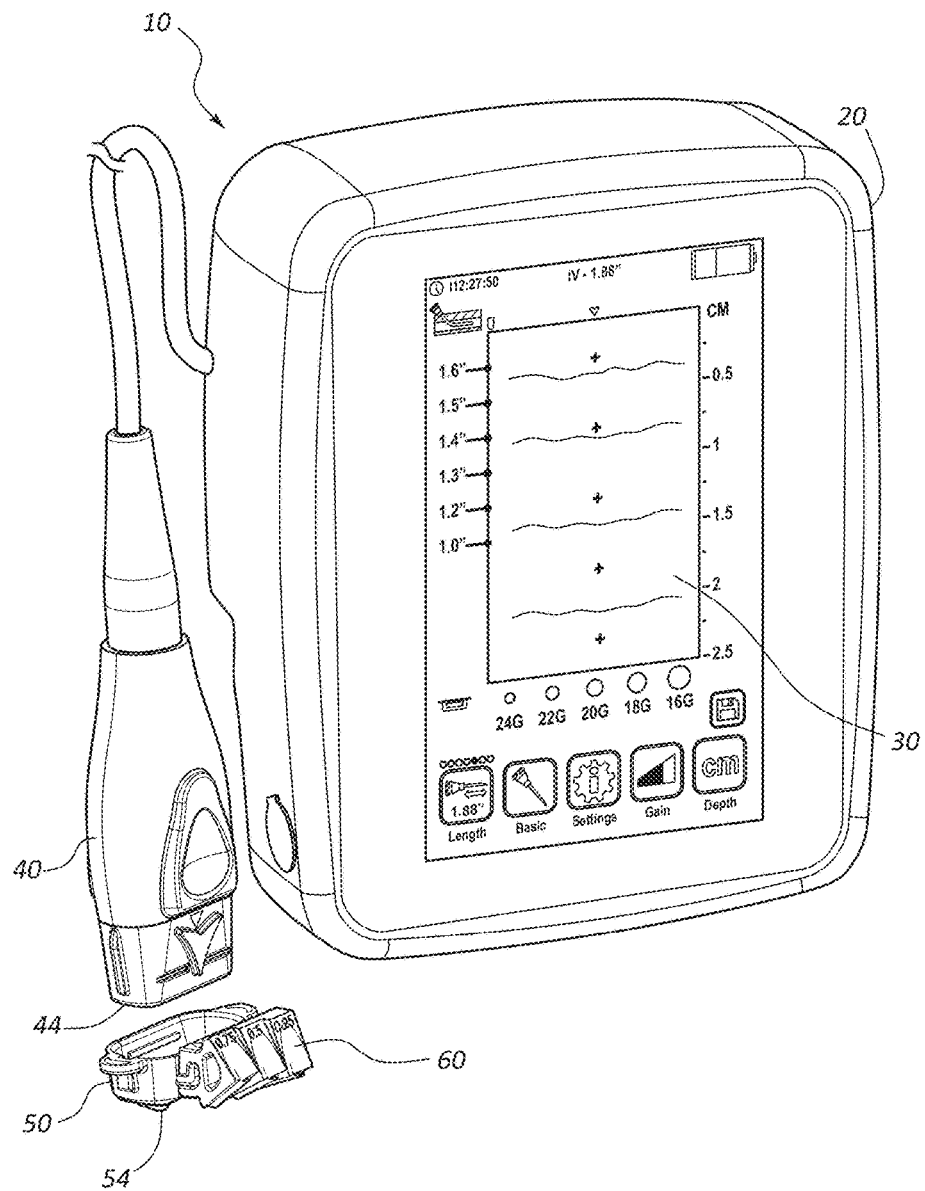
FIG. 1 is a perspective view of a portable ultrasound imaging system that serves as one possible environment in which embodiments of the present invention can be practiced.

FIG. 1 shows various components of an ultrasound imaging system 10, according to one embodiment. As shown, the system 10 includes a console 20 housing various electronic and other components necessary for processing and depicting ultrasonic images. The console 20 includes a touch-screen display 30 for depicting ultrasonic images and for enabling touch-based input by a clinician to control the device and its functionality. A probe 40, containing one or more transducer elements in a head 44 thereof for emitting and receiving ultrasonic signals, is operably attached to the console 20 via a cable or other suitable interface.

An optional cap 50 is shown for removable attachment to the head 44 of the probe 40 so as to cover the transducer elements disposed therein. The cap in one embodiment includes a hydrogel insert for providing an ultrasonically transparent interface between the probe head 44 and the skin surface. A needle guide 60 is slidably attached to the cap 50 to assist with guiding needles through the patient's skin and into the vessel being imaged by the system 10. Further details regarding the probe cap, hydrogel insert, and needle guide can be found in U.S. Pub. No. 2011/0313293, filed Aug. 9, 2011, and entitled "Support and Cover Structures for an Ultrasound Probe Head," and U.S. Pat. No. 9,788,812, filed Jun. 22, 2012, and entitled "Needle Guide with Selectable Aspects." Each of the foregoing applications is incorporated herein by reference in its entirety. Note that other ultrasound imaging devices and systems that differ from that shown here can also benefit from the embodiments described herein.

Figure 2:
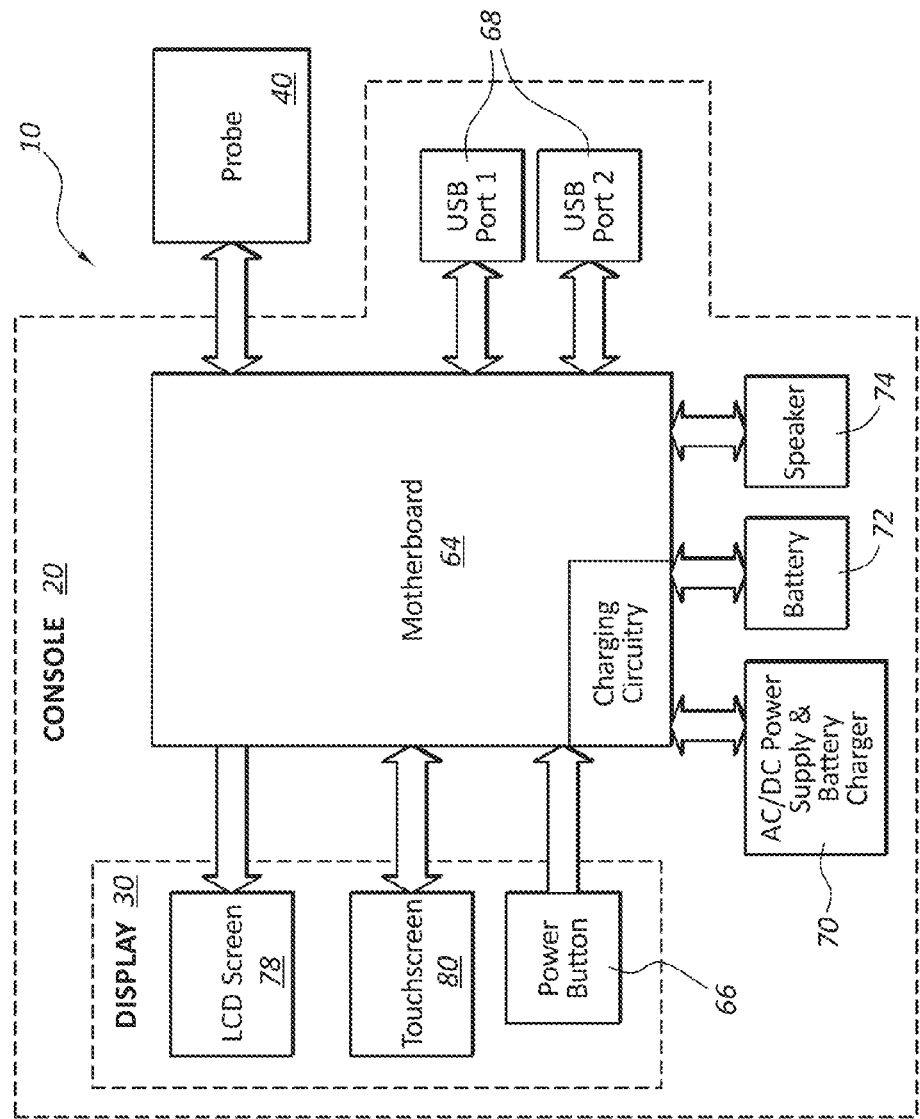
FIG. 2 is a block diagram showing various components of the ultrasound imaging system of FIG. 1.

FIG. 2 shows a block diagram of the system 10 of FIG. 1, according to one embodiment. In detail, the console 20, display 30, and probe 40 are represented, as in FIG. 1. The console 20 includes therein a motherboard 64 for governing system functionality and includes a processor or other general or special purpose computer, memory, storage locations, and other components for system operation. A power button 66 is included, as are USB ports 68 for interfacing with other devices. An external power supply 70, as well as a battery 72 and speaker 74, are provided for operation. The display 30 in the present embodiment includes an LCD screen 78 or other suitable screen, and a touchscreen 80 to enable touch-based functionality via the display 30. Note that the system 10 can include different, fewer, or more components than those listed here, including those components that enable the system to operate in a networked manner with other local or remote computing or network systems.

Figure 3:
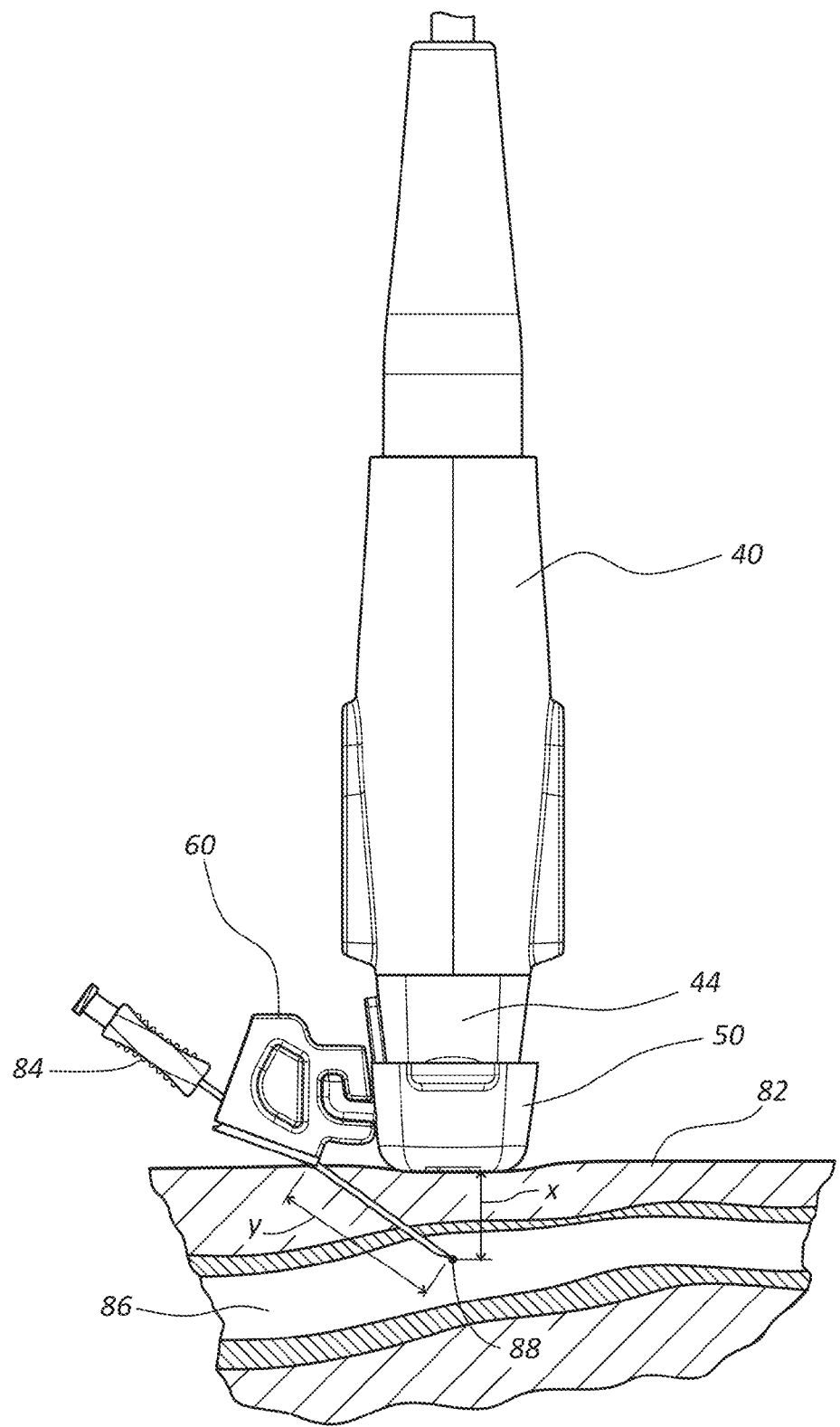
FIG. 3 is a cross sectional side view of an ultrasound probe of the system of FIG. 1 during use.

FIG. 3 shows use of the system 10 in accessing a vessel 86 with a needle 84 in preparation for inserting a catheter into the vessel. The probe 40, equipped with the head-covering cap 50 and attached needle guide 60, is placed against the skin so as to ultrasonically image a slice of internal body tissue of the patient below the surface of the skin 82. Indeed, a target location 88 of the vessel 86 imaged by the probe 40 is disposed a substantially vertical depth x below the end of the probe, corresponding to the skin surface 82. Though shown here as a central portion of the vessel 86, the target location 88 can be any one of various subcutaneous locations within the body.

The needle 84, disposed in the needle guide 60, follows an angled catheter insertion path a distance y to intercept the target location 88. This catheter insertion path, initially defined by the needle 84, is the same path to be followed by the catheter in order to gain access to and enter into the vessel 86. The vertical depth x from probe head 44 to the target location 88 can be calculated by a processor or other suitable component of the motherboard 64 of the system 10. Further, the system 10 can be loaded with appropriate data to know the distance y of the catheter insertion path to reach a given target location 88 at a depth x. In the present embodiment, these data are known by virtue of the position of the needle guide with respect to the probe head 44 and the angles in which the needle 84 can be oriented in the needle guide 60 in order to enable the needle to intercept the target location 88. As mentioned, such data can be loaded into the system memory for use by the processor during ultrasonic imaging, as will be described. In another embodiment, the system computes the distance y in real time based on the vertical depth x and other relevant factors.

Figure 4:
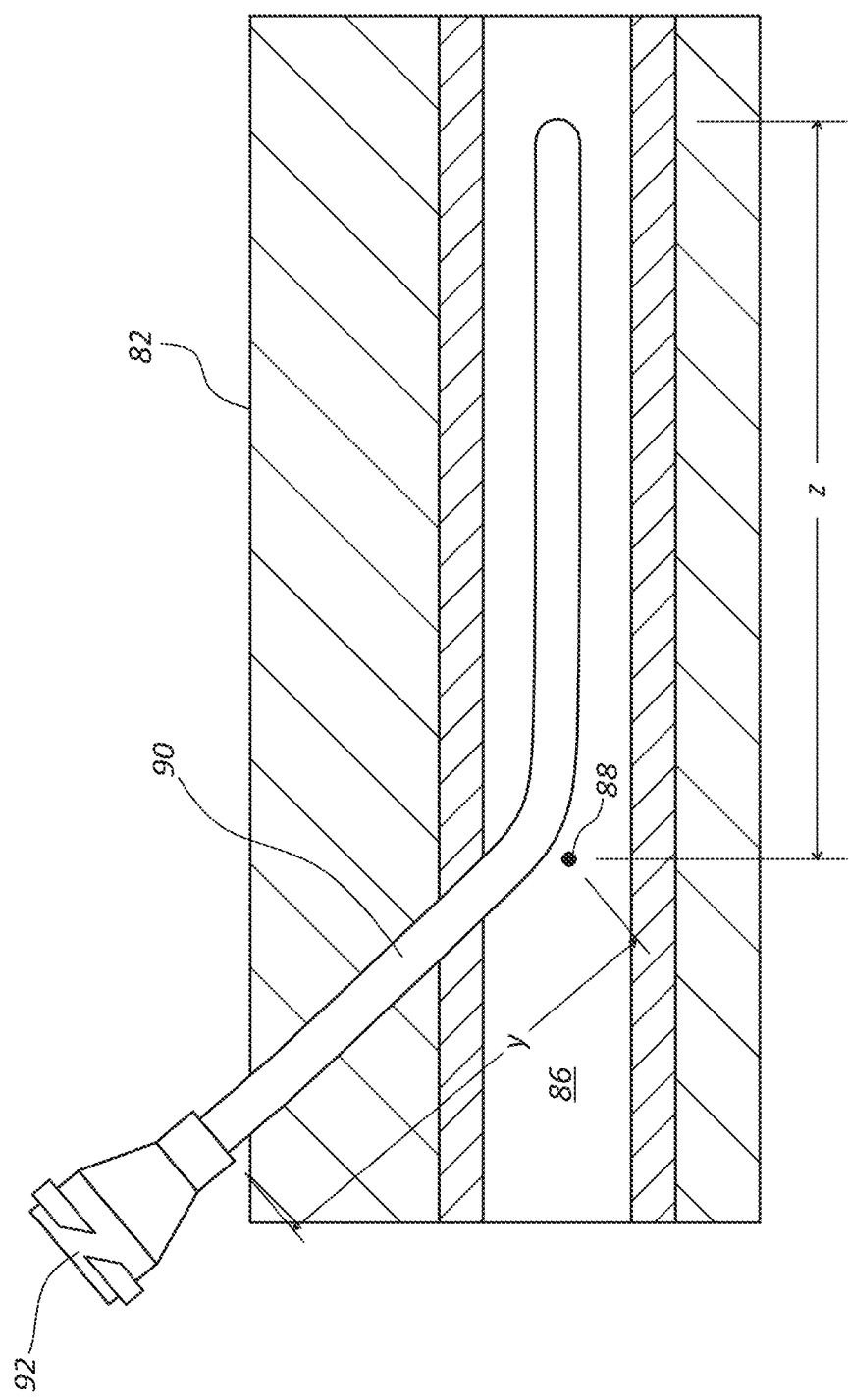
FIG. 4 is a cross sectional side view of a catheter disposed in a vessel.

FIG. 4 shows a catheter 90, including a hub 92, disposed along the catheter insertion path (FIG. 3) of length y so that a distal portion of the catheter corresponding to a length z is disposed within the vessel 86, approximately extending from the target location 88. So disposed, the catheter hub 92 is positioned proximate the skin surface 82. In accordance with one embodiment, the system 10 is configured to inform a user prior to catheter placement how much of a catheter of a given overall length will be disposed in the vessel 88 after placement is complete. The length of the catheter portion disposed within the vessel 88 is indicated in FIG. 4 by z. This in turn enables a user of the system 10 to choose an appropriate catheter length prior to actual insertion of the catheter into the patient so as to ensure that a sufficient portion of the catheter is disposed within the vessel. Note that while the following discussion focuses on placement of a catheter into a vessel, the principles described herein can be applied to the placement of other elongate and various medical devices, including various needles, catheters, access ports, etc.

Figure 5:
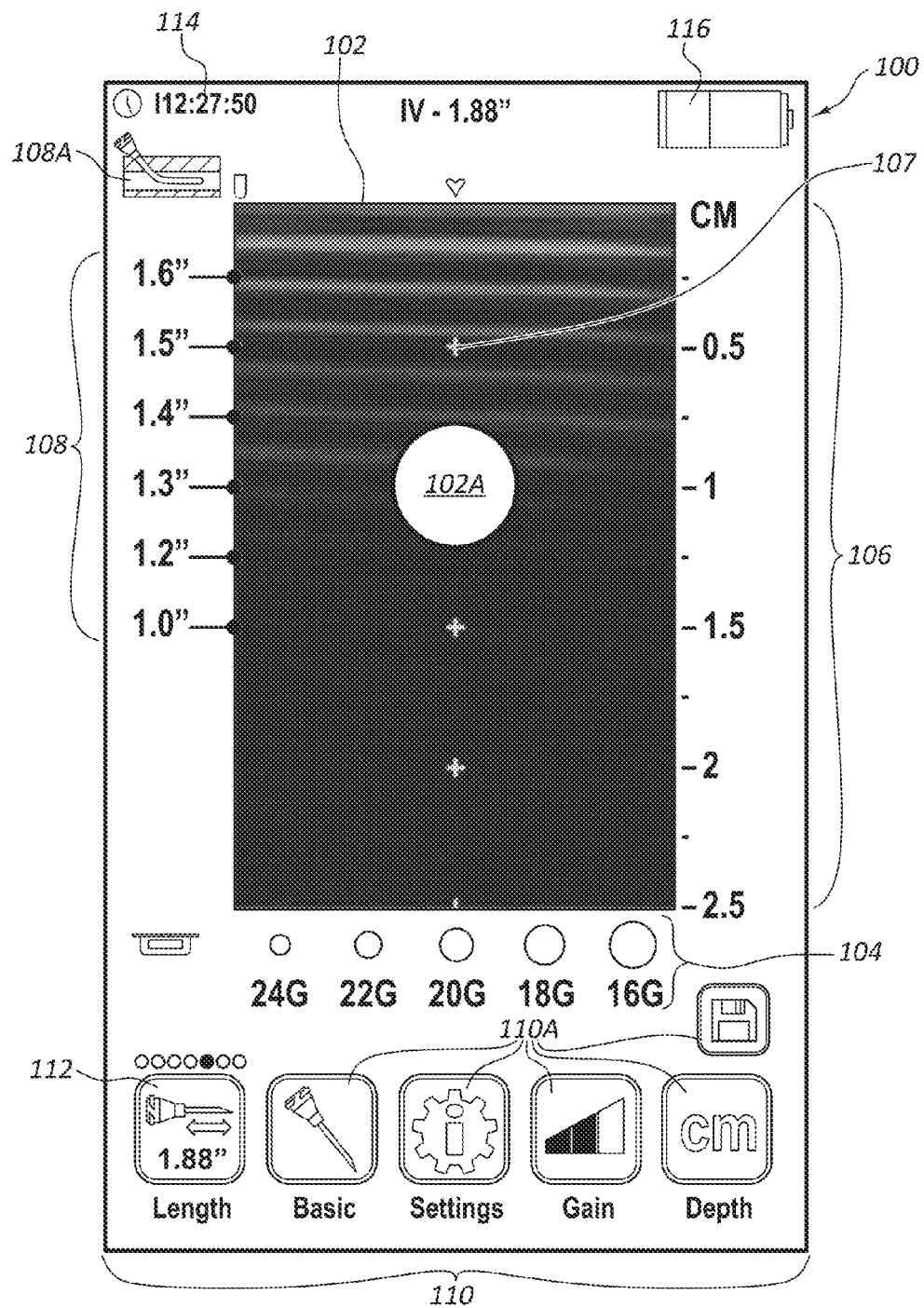
FIG. 5 shows a depiction on the display of the system of FIG. 1 according to one embodiment.

FIG. 5 shows a depiction 100 as depicted on the display 30 of the ultrasound imaging system 10 (FIG. 1) during operation thereof. An ultrasound image 102 is shown, including an image 102A of a vessel in cross section. The imaged vessel 102A shown here corresponds to the vessel 86 shown in FIG. 3, for example, though it is appreciated that the imaged item can be one of a variety of types of subcutaneous body features. A gauge icon field 104 is disposed below the ultrasound image 102 and includes a plurality of icons that each represent a cross sectional size, in gauge, of a catheter of the indicated size that is commonly available for insertion into the vessel via a catheter placement procedure. This assists the user in ascertaining an appropriately gauged catheter for insertion into the vessel represented by the vessel image 102A on the ultrasound image 102. Also shown are depth demarcations 106 (in cm) arranged along the image right border and corresponding depth markers 107 superimposed on the image 102 itself to assist the clinician in determining the depth of the vessel image 102A or other imaged feature. Note that the motherboard 64 (FIG. 2) or sub-component thereof determines the depth of the vessel image 102A, indicated at x in FIG. 3 as discussed. The depth of the vessel represented by the image 102A is readily seen by consulting the depth demarcations 106 to the right of the ultrasound image 102

As mentioned, the icons of the gauge icon field 104 represent cross sectional gauge sizes of, in this embodiment, various peripheral IV ("PIV") catheters used for providing vascular access to a patient. The gauge icons are color coded in accordance with a standardized color coding scheme that indicates the particular size of various PIV catheters. As will be seen, however, the icon field 104 can include color-coded icons representative of other medical devices designed for insertion into the patient body, such as dialysis catheters, blood draw needles, guidewire devices, port access needles, arterial lines, etc. Thus, the size, shape, and color of the icons can vary according to the catheter or other medical device the icons are configured to represent. As such, the discussion here should not be understood to limit the present disclosure in any way. Also, the particular colors shown can vary according to need, desire, convention, device type, etc.

In one embodiment, it is appreciated that the size of the icons in the field 104 can vary according to the scale of the ultrasound image 102 as to preserve a 1:1 size ratio therebetween. For example, the user of the system 10 can selectively increase the magnification of the ultrasound image 102 to double its previous size. When this occurs, the system 10 includes functionality to correspondingly scale, or alter the size of, the icons in the field 104 such that the icon size as depicted corresponds with the size of the vessel image 102A and other imaged features depicted on the display 30.

In another embodiment, the system 10 is configured to change the depth markers 107 to a particular icon when that icon is touched or otherwise selected by the user on the display 30. For instance, if the "20G" icon of the field 104 is pressed on the display 30 by the user, each of the four depth markers 107 that are overlaid atop the ultrasound image 102 will temporarily be replaced by a gauge icon of identical size and color as the "20G" icon of the icon field 104. This places the corresponding gauge icon in close proximity to the vessel image 102A and thus enables the user to more easily see how much of the vessel would be occupied by the selected catheter gauge size. The icon replacement of the depth markers 107 would last for a predetermined time, such as three seconds, in one embodiment, though this can be varied. In another embodiment, the icons can replace the depth markers indefinitely, or until user input deselects them.

In accordance with the present embodiment, FIG. 5 also gives details regarding the ability of the system 10 in one embodiment to provide information to the user regarding the amount of a catheter or other elongate medical device that can be disposed within the imaged vessel prior to actual catheter insertion into the vessel. As shown on the depiction 100 of FIG. 5, an in-vessel catheter length field 108 is shown on the left border of the ultrasound image 102, indicating the length of the portion of the catheter that would be disposed within an imaged vessel disposed at a plurality of discrete depths depicted in the image. When the system is in the in-vessel catheter length mode, an icon 108A is displayed on the display 30 together with the in-vessel catheter length field 108. Note that the display also depicts a clock icon 114 and a battery level indicator 116, though other icons/information can be optionally depicted on the display.

The particular in-vessel lengths shown in the field 108 are dependent upon the total catheter length selected, which is shown in a catheter length selection button 112 residing in a control button field 110 below the gauge icon field 104, though other locations are possible. The control button field 110 also contains additional control buttons 110A to govern other system processes, such as system settings, saving the ultrasound image, etc. As shown in the present example of FIG. 5, the total catheter length as indicated by the catheter length selection button 112 is 1.88 inches; thus, each of the depths marked in the in-vessel catheter length field 108 indicate the length of the portion of the 1.88 inch-long catheter that would be disposed in a vessel located at the below-skin depth as indicated by the depth demarcations 106, i.e., the distance x on FIG. 3.

For instance, as shown in the ultrasound image 102 of depiction 100 of FIG. 5, the imaged vessel 102A is shown at about 1 cm in depth, as indicated by the image depth demarcations 106 on the right side of the image. The catheter length selection button 112 indicates that a 1.88 inch total-length catheter has been selected. Thus, for a 1.88 inch total-length catheter, the user can see from the in-vessel catheter length field 108 disposed on the left side of the ultrasound image 102 that approximately 1.3 inches of the catheter would be disposed within the imaged vessel 102A if the catheter were to be inserted therein. As seen in FIG. 4, the remainder portion of the catheter would be taken up by the angled insertion path (indicated by y) between the skin surface 82 and the target location 88 where the catheter enters the vessel wall. Note that this information is provided before the catheter is inserted, thus enabling the clinician to select the proper catheter length before vascular access is attempted. As noted above in connection with FIG. 3, the ability of the system 10 to calculate the depth x of the vessel, together with knowledge of the length y of the needle/catheter insertion path, enables the system to determine the amount of catheter length to be disposed within the vessel 86 beginning at the target location 88 for a catheter inserted along the insertion path, prior to actual catheter insertion.

Figure 6:
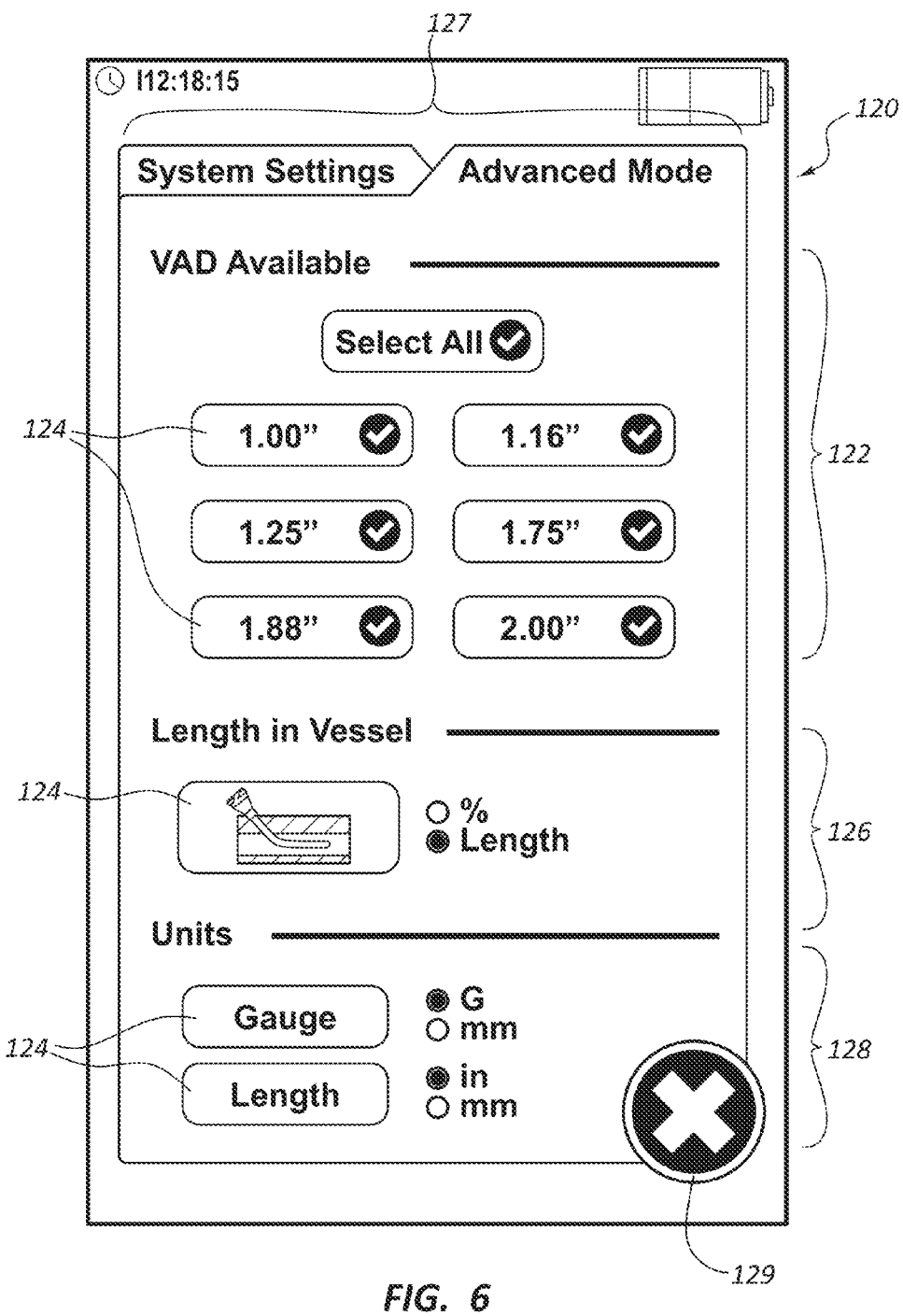
FIG. 6 shows a depiction on the display of the system of FIG. 1 according to one embodiment.

The overall length of the catheter represented and depicted by the system 10 can be selected by the user, in the present embodiment. FIG. 6 shows a depiction 120 as one example of an interface that enables the user to select one or more possible catheter lengths that can be toggled through by the user in order to select a catheter having sufficient length to reside within the imaged vessel. In particular, the depiction 120 of FIG. 6 shows a touchscreen interface including a catheter length selection field 122 listing the available catheter lengths as buttons 124 that can be toggled on or off by the user. If a particular catheter length option is toggled off, the user will not be able to select that length as an option via the catheter length selection button 112 on the depiction 100 of FIG. 5. Also shown in the depiction 120 is a length-in-vessel unit selection field 126 to show the amount of catheter in the vessel in either a length measurement or as a percentage of overall catheter length, and a unit selection field 128 to select the dimensional units for the gauge and catheter length. Thus, it is seen that the touch screen interface shown here enables a clinician to select which available catheter lengths can be used by the device 10 to calculate the length of the catheter residing within the vessel when the catheter is disposed therein. Once the present depiction is cancelled and the depiction 100 of FIG. 5 returns, the overall catheter length indicated in the catheter length selection button 112 defaults to the smallest catheter length among those previously selected from the field 122 of FIG. 6, in one embodiment.

Figure 7:
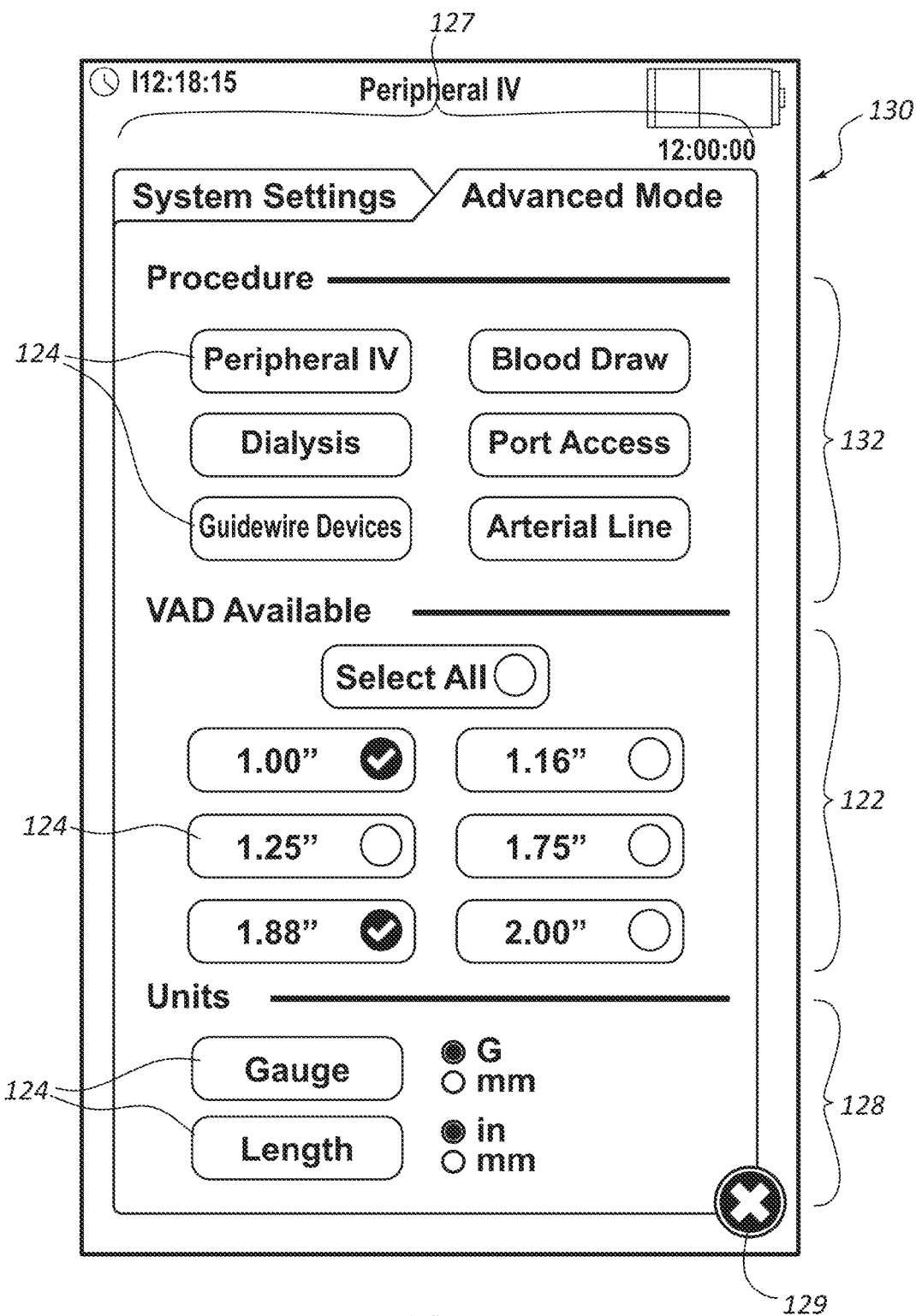
FIG. 7 shows a depiction on the display of the system of FIG. 1 according to one embodiment.

FIG. 7 shows a depiction 130 disclosing another possible user interface for selecting operational aspects of the system 10. In addition to the catheter length selection field 122 and units selection field 128 already discussed, the depiction 130 includes a procedure selection field 132, where a user can select which type of procedure for which the system 10 will be used in assisting in the placement of a medical device into the body of the patient. Such procedures include PIV, dialysis, blood draw, etc., and employ catheters or needles. This enables the user to select the desired procedure, which then enables the system 10 to depict the procedure-specific gauge icon field 104 and to depict in the length selection field 122 the available lengths of catheters or needles to be used for the procedure, which lengths can be selected by the clinician, as just described. The selected lengths will then be available for call-up on the display 30 during the procedure via the length selection button 112 shown in FIG. 5 and used in a manner similar to that described above in connection with that figure. As such, the system 10 and associated methods described herein can be employed for a variety of procedures involving vascular access by a medical device, including devices not explicitly set forth herein.

Reference is now made to FIG. 8, which depicts a lookup table 140 used by the system 10 in displaying the in-vessel catheter lengths shown in the in-vessel catheter length field 108 (FIG. 5) in accordance with one embodiment. As shown, the table 140 includes a set of possible catheter length values 142, which correspond with the available catheter lengths shown in the catheter length selection field 122 of FIGS. 6 and 7. Note that in the embodiment of FIG. 6, only one procedure, i.e., peripheral IV catheter insertion, is selectable on the system 10; as such, only one lookup table, e.g., table 140 of FIG. 8 is included in the system. In the embodiment shown in FIG. 7, multiple procedures are possible, as shown in the procedure selection field 132; thus, one lookup table for each procedure may be included in the system 10 in this case. In one embodiment, the lookup table 140 is stored in a memory/storage location located on or in operable communication with the motherboard 64 (FIG. 2).

The table 140 of FIG. 8 further includes a set of needle guide depth values 144 that indicate the angle and depth at which a catheter, such as the catheter 90 shown in FIG. 4, will intercept a target location, such as a vessel as indicated by the target location 88 shown in FIG. 3. The values 144 shown in FIG. 8 thus represent the target location depth x (FIG. 3). As it assumes that the catheter will be inserted along the angled insertion path of length y, which path is first established via insertion of a needle through the needle guide 60, the system 10 regards the depths listed in 144 as accurate.

Thus, when a user selects a particular overall catheter length via the catheter length selection button 112 (FIG. 5) during imaging of a vessel, the system 10, via its motherboard processor or other suitable component, can access the lookup table 140 for the selected catheter length. Then, for each of the listed target location depth values 144, the system 10 can depict a corresponding column of the length-in-vessel values 146, which each indicate the length of the portion of the catheter that would reside within the imaged vessel if the catheter having the selected overall length (set 142) were placed in a vessel at the target location at the corresponding depth (set 144). These length-in-vessel values are also referred to herein as proximity information or data.

These length-in-vessel values 146 for the selected overall catheter length are then depicted on the display 30 in the in-vessel catheter length field 108 as shown in FIG. 5, or in some other suitable location. With this and the other information depicted on display 30 of FIG. 5, the user can decide whether the currently selected catheter is long enough to suitable dwell in the imaged vessel 102A. If not, the user can press the catheter length selection button 112 and change the selected catheter length while continuing to image the vessel 102A. The system will then access the lookup table (FIG. 8) and acquire the length-in-vessel values 146 that correspond to the newly selected overall catheter length from the possible lengths 142. The display 30 will be refreshed to depict the new length-in-vessel values in the in-vessel catheter length field 108 for each of the depth values 144 of the table 140. Note that the number of possible depth values 144, overall catheter length values 142, and corresponding length-in-vessel values 146 can vary according to type of procedure, size range of catheters, type of medical device to be inserted, etc.

Figure 9A:
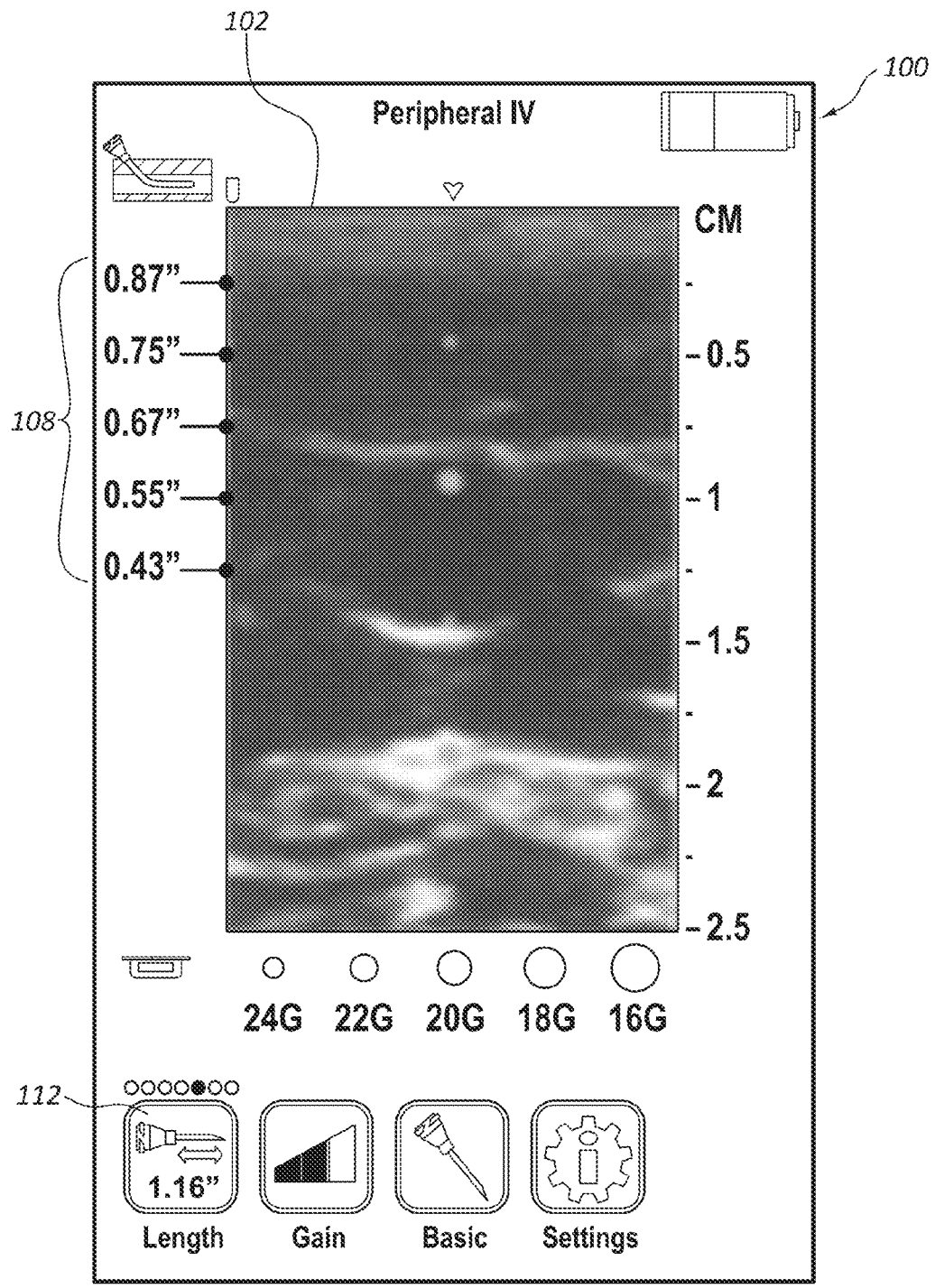
FIGS. 9A-9C show various depictions on the display of the system of FIG. 1 according to one embodiment.
Figure 9B:
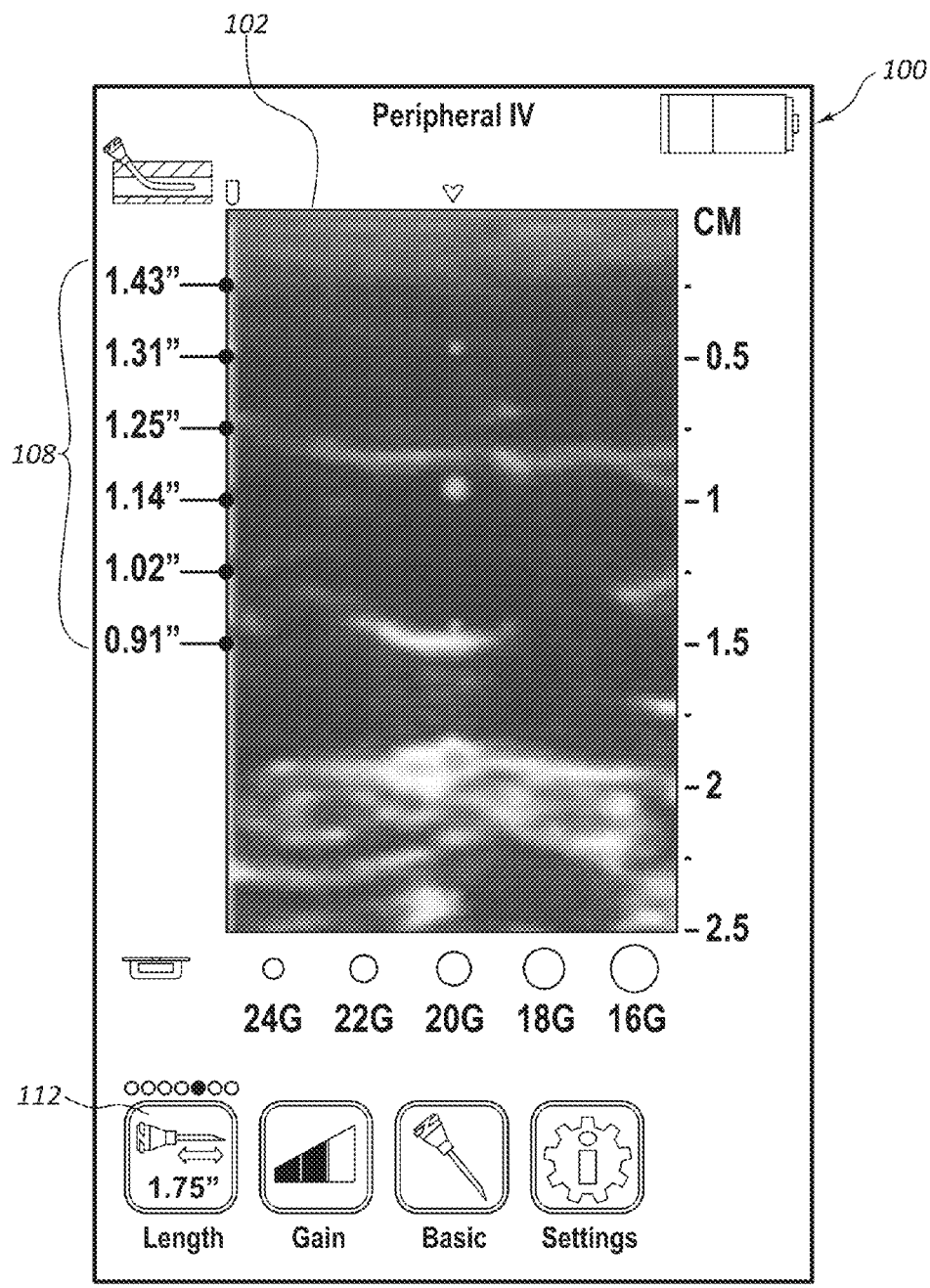
Figure 9C:
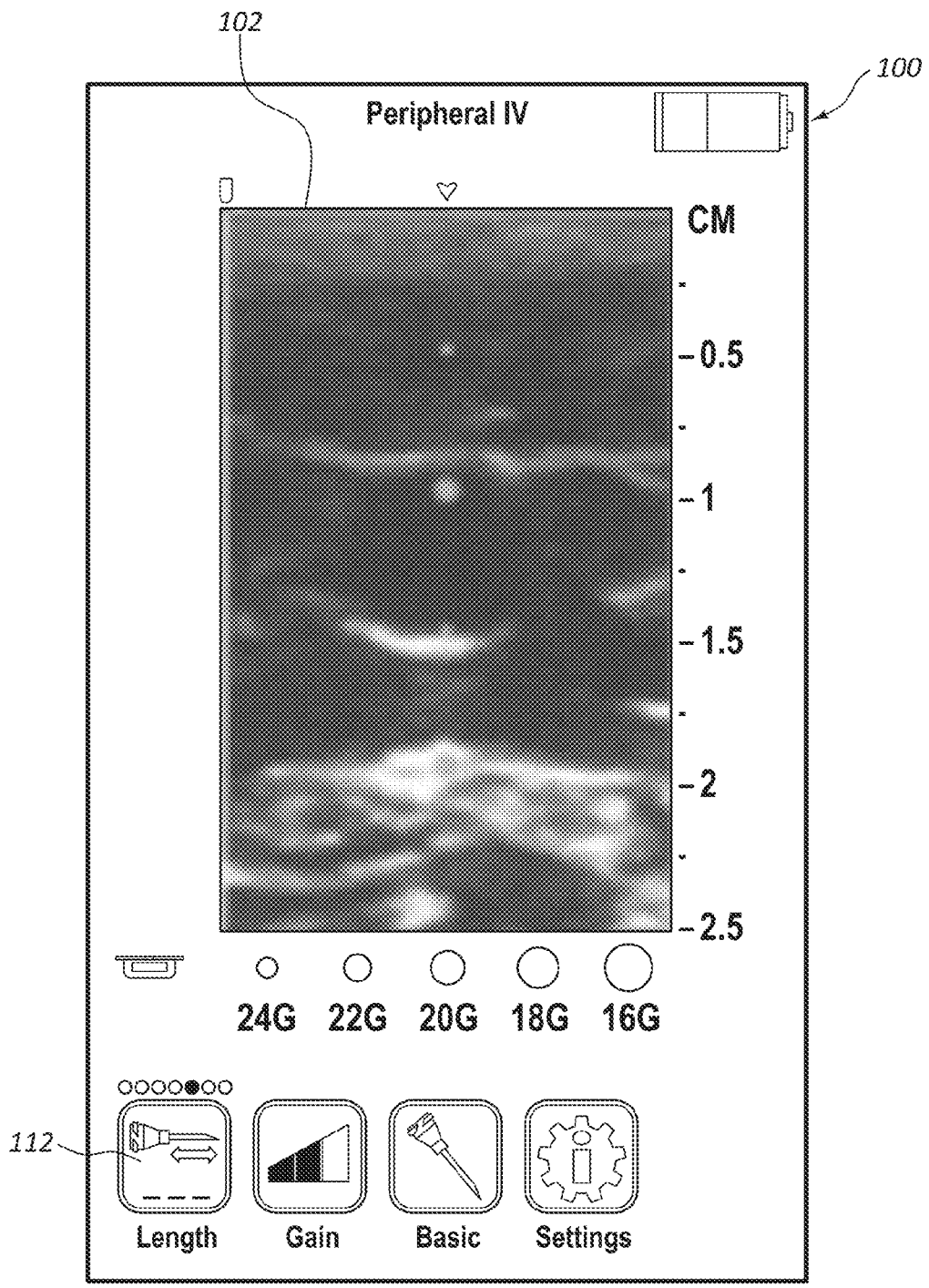

As mentioned above, during use of the system 10 the user can toggle between the various catheter lengths, previously selected via the interface shown in the depictions of FIG. 6 or 7 for example, in order to determine the amount of catheter (or other suitable medical device) that will remain in the vessel after placement thereof. FIGS. 9A-9C show one example of such toggling, wherein the catheter length is selected by the clinician via successive pressing of the catheter length selection button 112, which toggles between the length selections of 1.16 inches (FIG. 9A), 1.75 inches (FIG. 9B), and no selected catheter length (FIG. 9C). As further shown in FIGS. 9A-9C, the amounts of catheter length in the vessel as seen in the in-vessel catheter length field 108 vary according to the particular catheter length selected, corresponding with the data in the lookup table 140 of FIG. 8. Note that when no catheter length is selected in the selection button 112, the in-vessel length field 108 is unpopulated. Note further that the particular units shown for vessel depth, catheter length, etc. can vary from what is shown and described herein.

Figure 10:
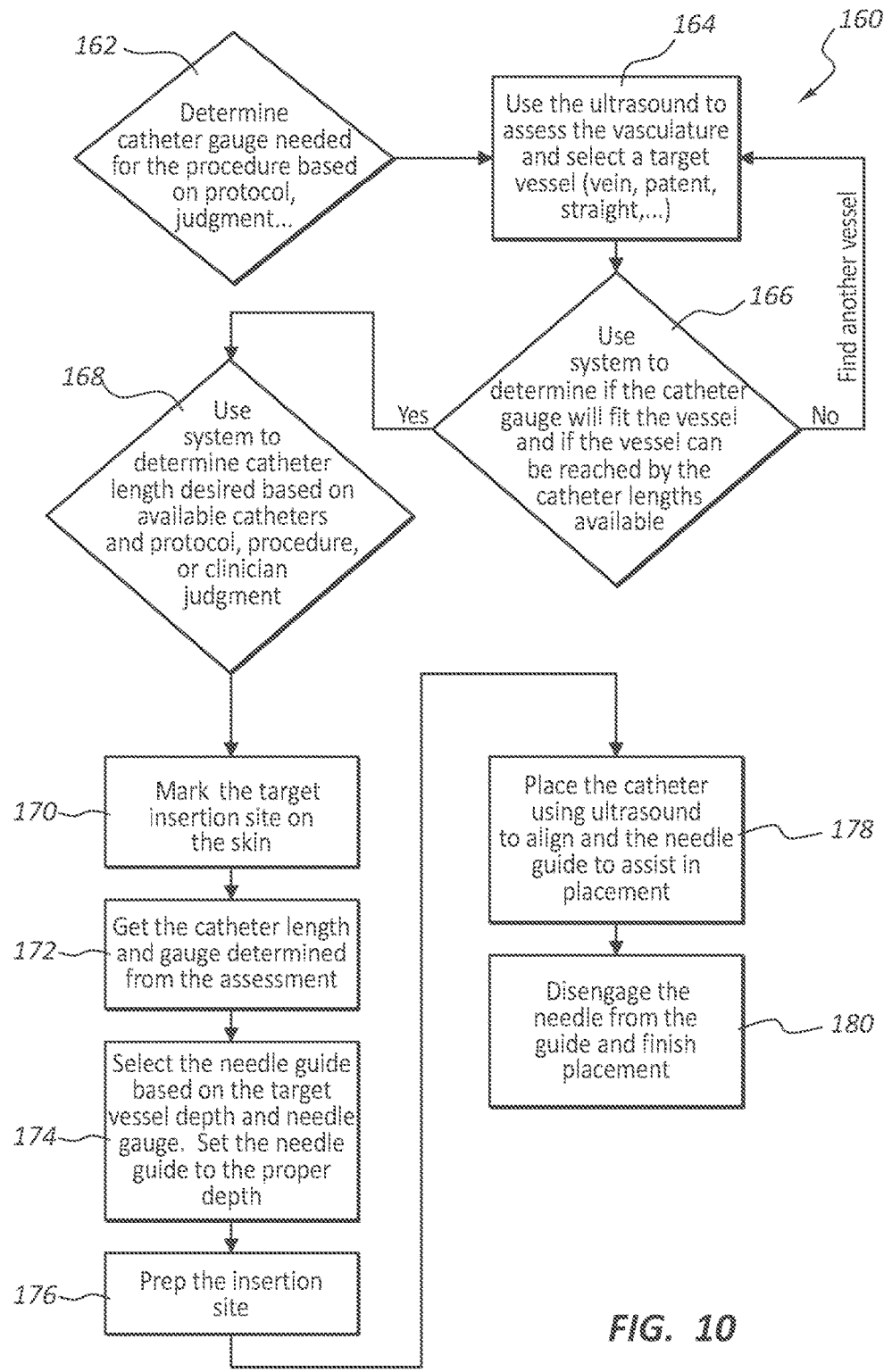
FIG. 10 shows a flowchart including various stages for the insertion of a medical device within the body of a patient, according to one embodiment.

FIG. 10 shows a flowchart 160 of a typical catheter insertion procedure using the system 10 and methods described herein. It is assumed here that a peripheral IV catheter insertion procedure will be performed. If more than one procedure can be assisted by use of the system 10, an initial selection of the desired procedure via procedure selection field 132 would be performed by using the interface depicted in the depiction 130 of FIG. 7. The selection of the desired units in which measurements are to be displayed (fields 126 and 128 in FIGS. 6 and 7) can also be made at this point, if necessary.

At stage 162, a user determines the catheter gauge needed for the catheter insertion procedure. At stage 164, the ultrasound imaging system 10 (FIG. 1) is employed to image a vessel or other subcutaneous object and determine a target location (FIG. 3). At stage 166, the system 10 is employed to determine whether the initially selected catheter gauge will fit in the imaged vessel and whether the vessel can be reached by any one of the available catheter lengths. If not, another vessel that meets these requirements is searched for.

If the answer to the inquiry at stage 166 is yes, stage 168 is executed wherein the system 10 is employed to determine an ideal overall catheter length that disposes a desirable portion of the catheter within the vessel, as has been described above in connection with FIGS. 3-9C and which conforms to any requirements or procedures of the user. At stage 170, a skin insertion site is marked, after which a catheter of proper overall length and gauge as previously indicated by the system 10 is acquired in stage 172. At stage 174, the particular guide channel of the needle guide (such as needle guide 60 of FIG. 3 that includes three guide channels for accessing three unique target depths) is selected so as to guide a needle to the proper depth to intercept the targeted vessel. Any necessary adjustment of the needle guide can be performed at this stage.

The skin insertion site is prepped at stage 176, and at stage 178 the peripheral IV catheter-equipped needle is inserted through the needle guide, into the patient's skin, and proceeds along the insertion path (FIG. 3) to intercept the targeted vessel and insert the catheter the desired distance into the vessel, as was anticipated and planned for prior to inserted by use of the system 10. The ultrasound imaging of the system 10 can be employed to help guide the needle into the vessel, in one embodiment. At stage 180, the needle is removed from the needle guide and the placement procedure is completed according to protocol.

FIG. 11 shows some of the common catheter/needle gauge sizes for example procedures with which the system 10 can be employed to assist in device placement, including peripheral IV catheter gauge icons 190, dialysis catheter gauge icons 192, blood draw needle gauge icons 194, an intermediate dwell catheter gauge icons 196. These icons can be depicted in the gauge icon field 104 (FIG. 5), as has been described. Note that many other catheters, needles, and other suitable medical devices can be placed using the system 10 as described herein.

Figure 12A:
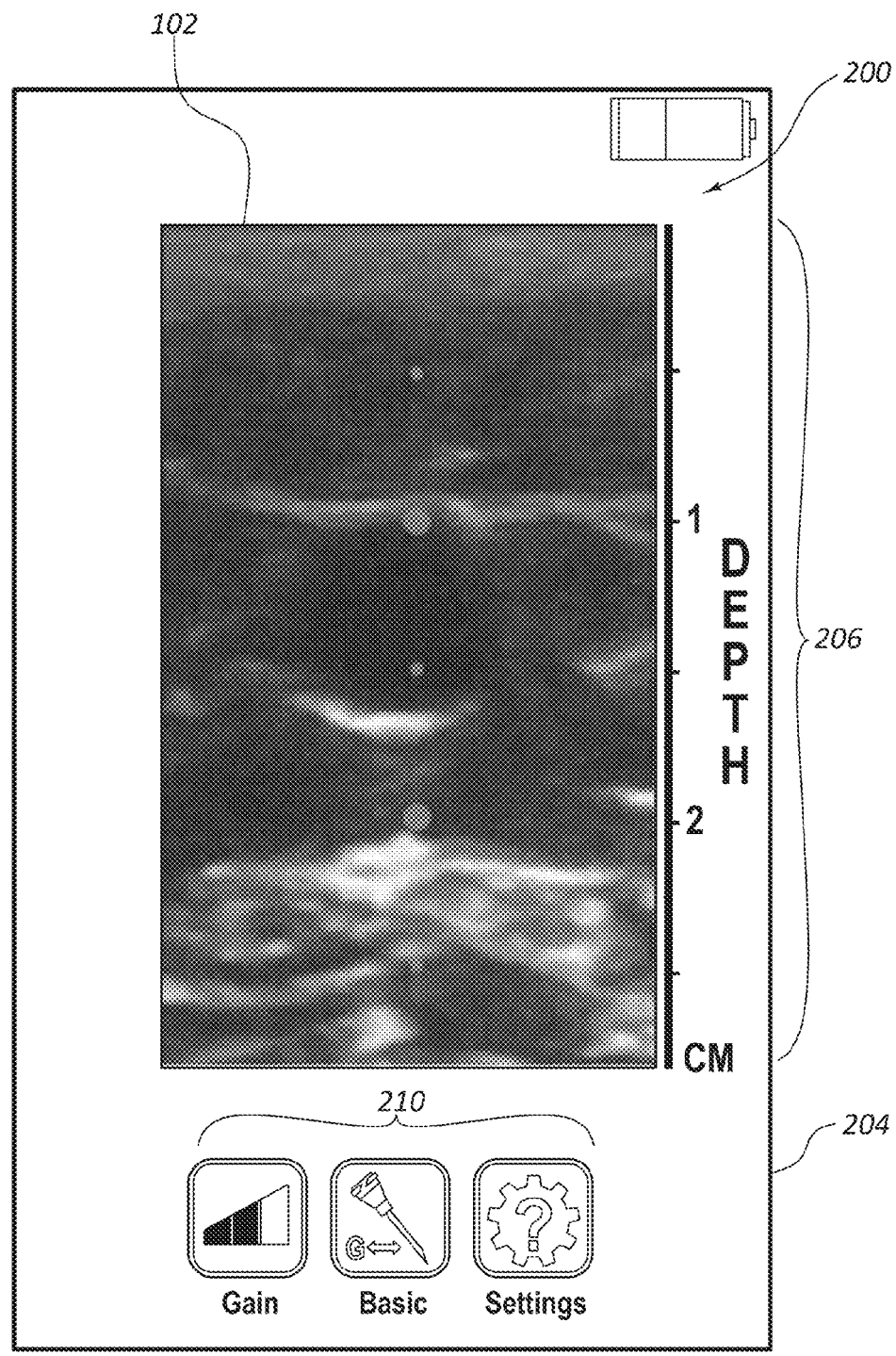
FIGS. 12A-12C shows various depictions on the display of the system of FIG. 1 according to one embodiment.
Figure 12B:
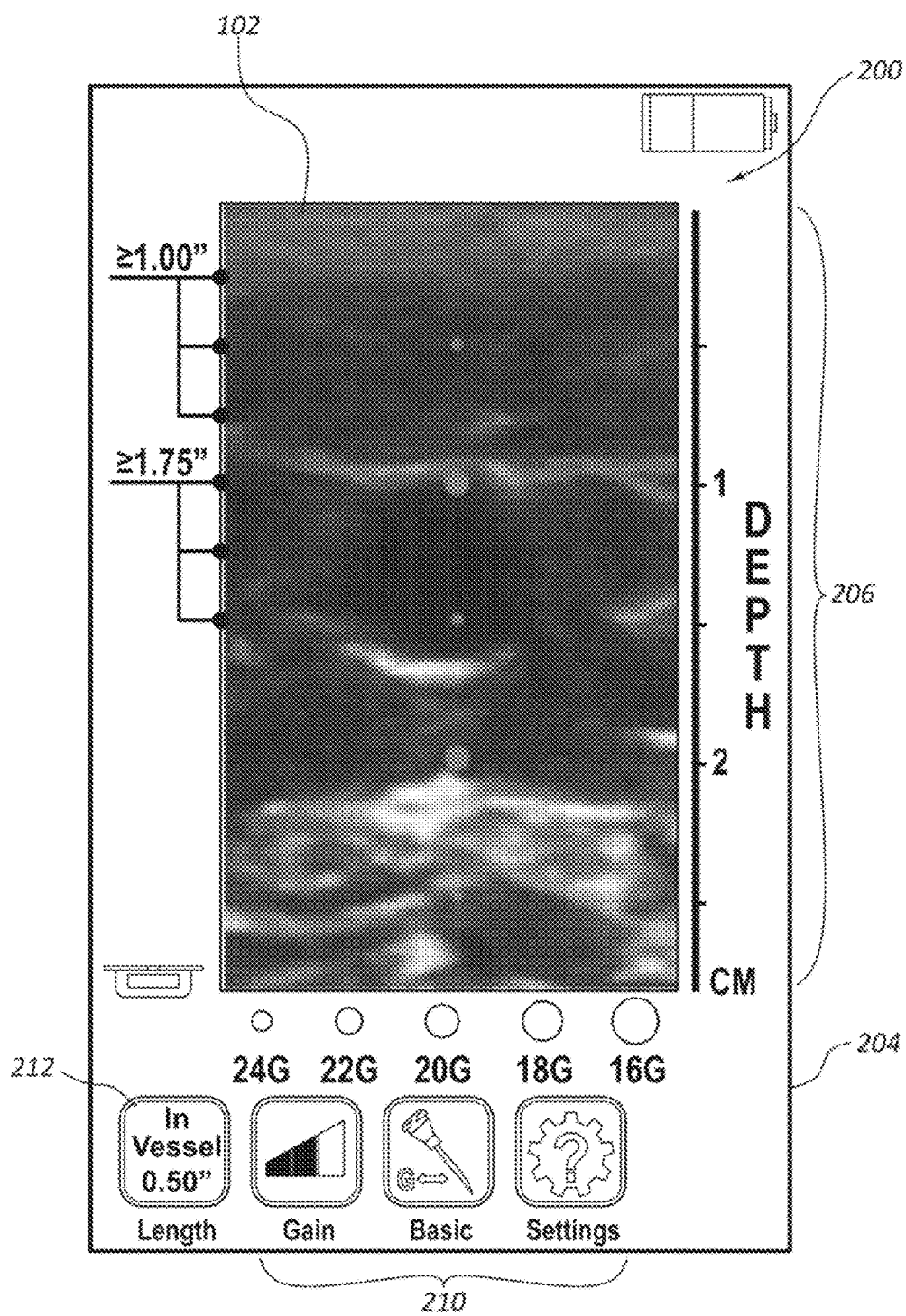
Figure 12C:
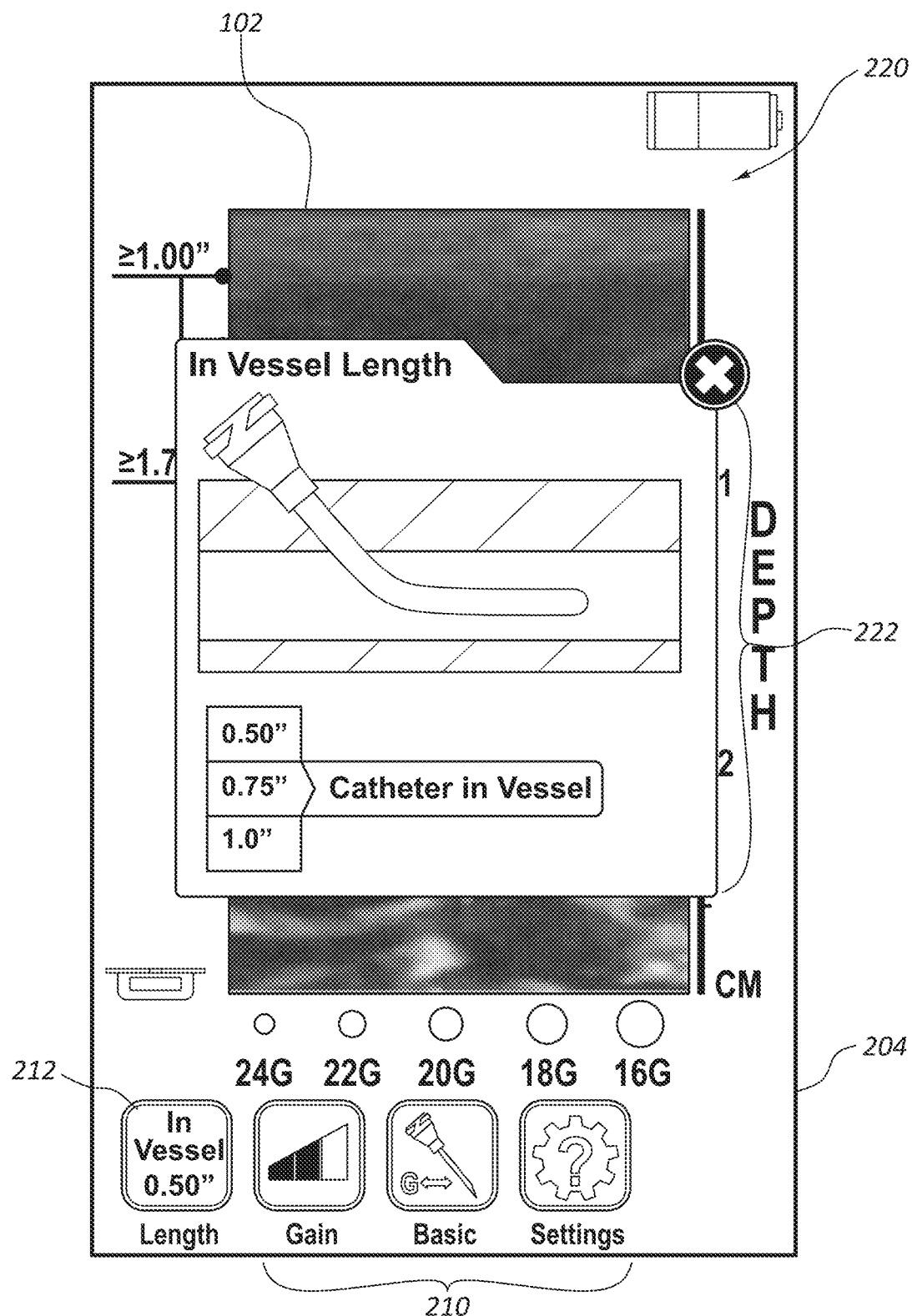

Reference is now made to FIGS. 12A-12C, which shows a depiction 200 of the present system according to another embodiment. The depiction is similar in various respects to previous depictions as shown in FIG. 12A, including the ultrasound image 102, an imaged vessel 102A, a control button field 210, depth demarcations 206, and a gauge icon field 204. In contrast to the above discussion in connection with FIGS. 3-9C, however, in the present embodiment the system 10 can be configured such that the user inputs the desired amount of catheter length to be disposed within the imaged vessel. This can be done in the present embodiment by toggling the catheter length-in-vessel selection button 212 shown in FIG. 12B. The system 10, having calculated the depth of the vessel (x in FIG. 3) and knowing the distance of the angled insertion path (y in FIG. 3), can then inform the clinician as to the catheter(s) having overall lengths sufficient to provide at least the desired length of catheter within the vessel. This information is displayed to the left of the ultrasound image 102 in a suggested catheter length field 208, as shown in FIG. 12B. FIG. 12C shows an optional depiction 220 wherein a catheter length-in-vessel selection field 222 is shown. Such a field would be employed by the user to select how much of a catheter to be placed would occupy the vessel interior. The selection made by the user from the selection field 222 would then be displayed in the catheter length-in-vessel selection button 212. Of course, other selection and depiction schemes for such user selections can be employed. Optionally, the system 10 in one embodiment can recommend only a single catheter having the best fit for the desired amount of catheter to remain in the vessel.

Figure 13:
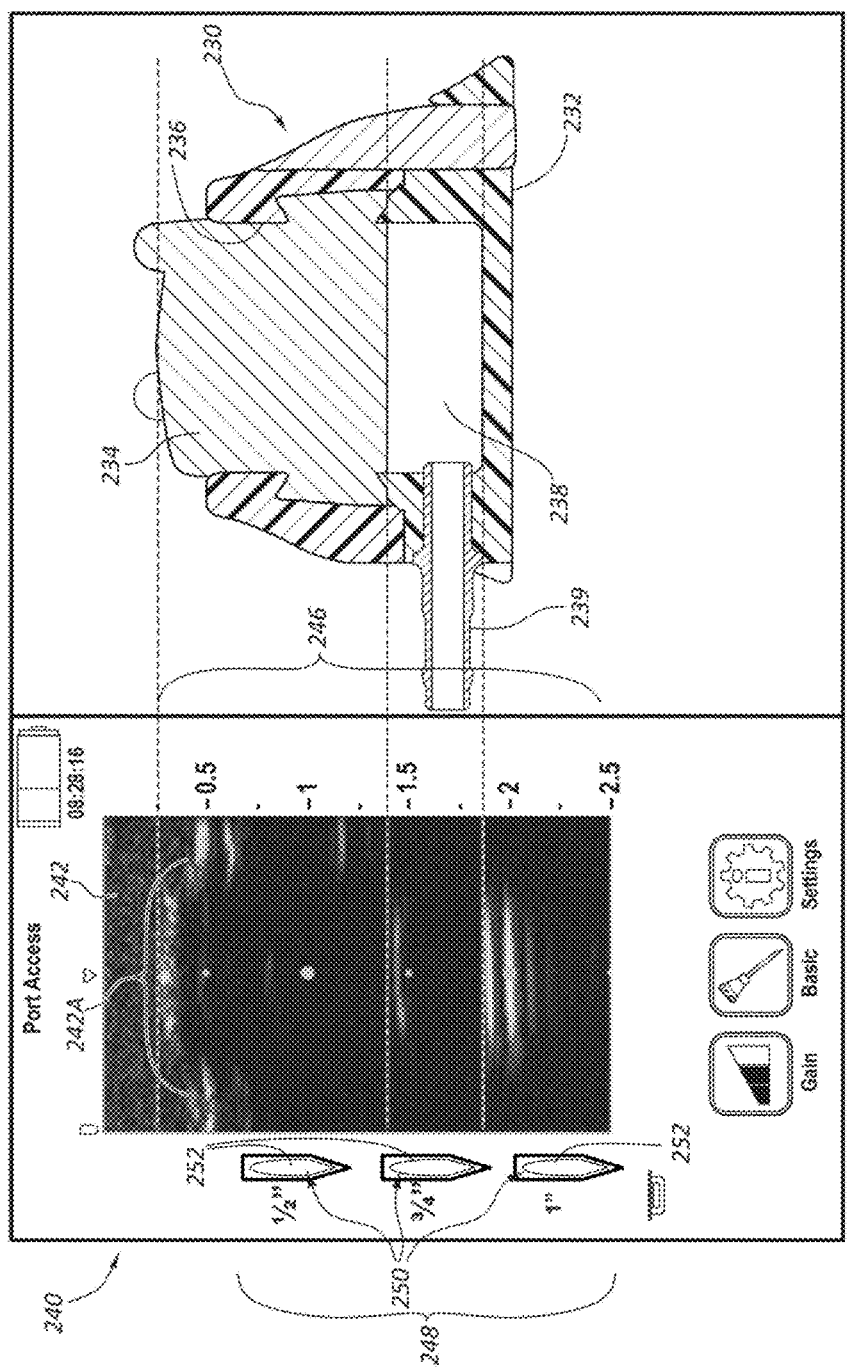
FIG. 13 shows a depiction on the display of the system of FIG. 1 together with a cross sectional view of an implantable access port according to one embodiment.

Reference is made to FIG. 13, which depicts use of the system 10 in inserting a needle into an implanted access port within the patient's body, according to one embodiment. An example access port 230 is shown on the right side of FIG. 13 and includes a body 232 and a septum 234 disposed in an opening 236 that is defined by the port body. The septum 234 provides needle-penetrable access to a reservoir 238. A stem 239 provides a fluid outlet for the reservoir 238. Thus, the access port 230 can be used in providing fluid medicaments to a patient by inserting a needle through the patient skin and into the septum 234 such that the distal opening of the needle resides within the reservoir. Fluid can then be passed from the needle distal opening into the reservoir 238, where it can then exit the reservoir through the stem 239 and pass into the patient body via a catheter connected to the stem.

On the left side of FIG. 13 is a depiction 240 from the display 30 of the system 10 according to the present embodiment. As shown, an ultrasound image 242 is depicted, which includes an image of a port 242A. The imaged port 242A in the ultrasound image 242 corresponds with the port 230, which is shown here for reference purposes. The various features of the port 230 can be seen ultrasonically in the ultrasonic port image 242A as indicated by the horizontal dash lines extending between the actual and imaged port, including the top of the septum 234, the bottom of the septum, and the bottom surface of the reservoir 238.

The depiction 240 includes depth demarcations on the right side of the ultrasound image 242 for use in determining the depth of the imaged port 242A under the patient skin. The depiction further includes a needle depth field 248 along the left side of the ultrasound image 242 that provides proximity information regarding possible needle lengths that may be used to access the implanted port. Particularly, the needle depth field 248 includes a plurality of needle depth icons 250 that can indicate to a user the depth to which select needles of different lengths would descend in accessing the imaged port 242A. The needle depth icons 250 are aligned next to the ultrasound image 242 to show how deep a needle of the indicated length would reach in accessing the imaged port 242A. Specifically, each needle depth icon 250 includes an image of a distal opening 252 of the needle which further assists the user in determining when the distal opening is sufficiently disposed within the port reservoir so as to suitably infuse fluids therethrough.

For instance, it is seen from the depiction 240 that a needle of length ½ inch piercing the skin and vertically pressed down into the imaged port 242A would not descend sufficiently far to penetrate through the bottom of the port septum, while a of ¾ inch length would successfully pierce the entire septum. Thus, the user is able to determine the proper length of needle to use in accessing the implanted port prior to needle insertion. This functionality is enabled by virtue of the ability of the system 10 to determine the depth of the implanted port and to visually distinguish the port features of interest, including the septum and the reservoir. In the present embodiment, the size of the needle depth icons 250 are scalable with the ultrasound image 242 in a 1:1 ratio so as to preserve the ability to determine a suitable needle depth. This embodiment thus serves as but one example of where the system 10 can be employed in assisting with the insertion of medical devices other than catheters. Other examples are also contemplated.

Figure 14:
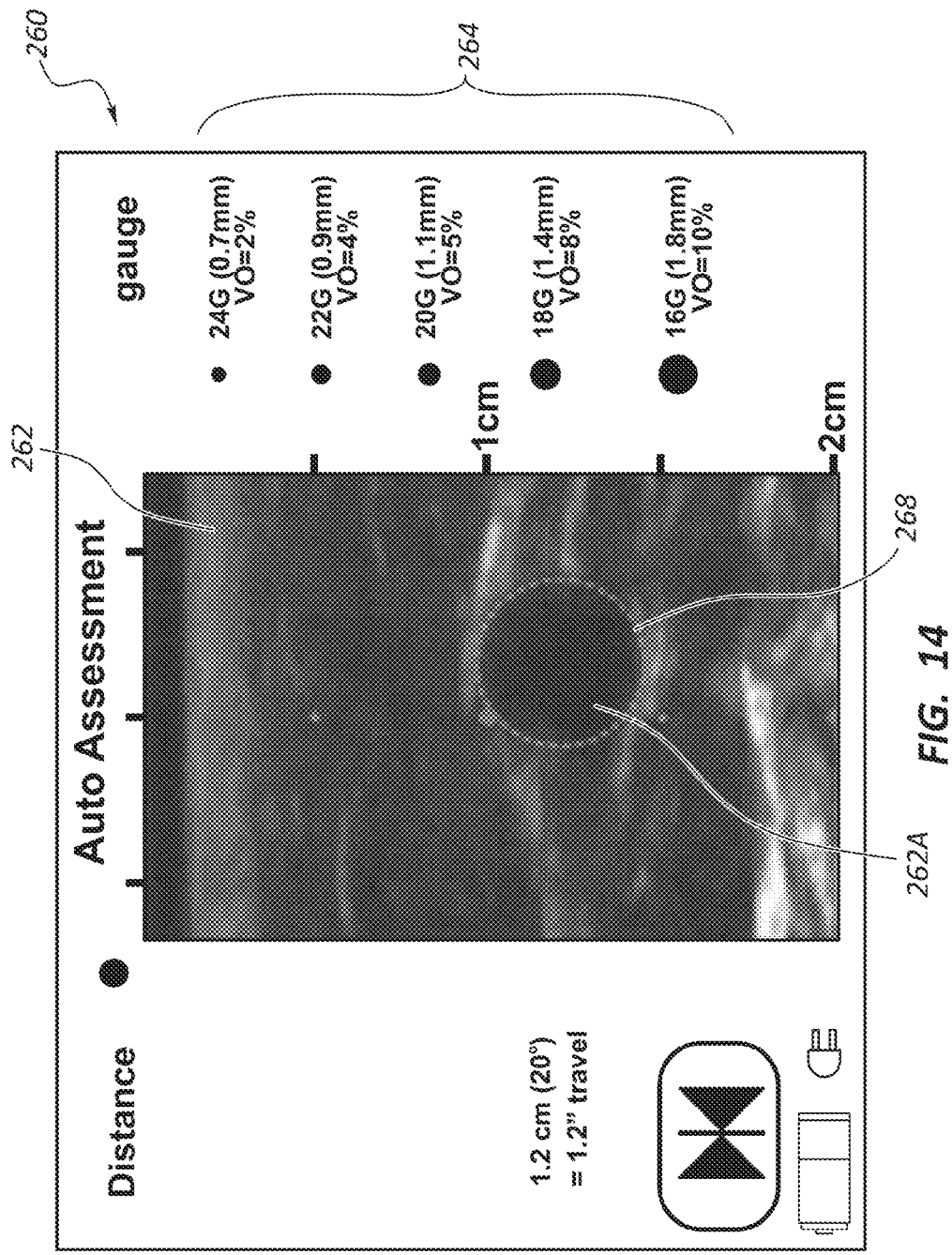
FIG. 14 shows a depiction on the display of the system of FIG. 1 according to one embodiment.

Reference is made to FIG. 14, which shows a depiction 260 by the display 30 of the system 10 according to one embodiment. As shown, the depiction includes an ultrasound image 262 and an imaged vessel 262A. A gauge icon field 264 is disposed to the right of the ultrasound image 262. In the present embodiment it is appreciated that a processor or other suitable component of the motherboard 64 of system 10 (FIG. 2) can execute one or more algorithms to automatically detect the presence of a vessel in the ultrasound image 262 captured by the system 10 during operation. These algorithms take advantage of the fact that blood vessels represent a rapid gradient change compared to surrounding tissue when viewed ultrasonically, due to the relative density difference between the two. Further, vessels are typically round and possess a relatively ultrasonically homogenous interior structure, which further assist algorithms in detecting vessels in an ultrasonic image.

In one embodiment vessel detection is an automated process. First, a data set represented by the ultrasonic image is presented for analysis. Vessel and tissue boundaries are detected via application of an edge detection filter, such as a Canny or Sobel filter. Convolution is then applied to the resultant data set of identified candidate vessels to map approximated centers of the vessels. Multiple circle kernels may be applied during convolution corresponding to known or likely vessel diameters.

Once the centers of the candidate vessels are determined, a radially expanding edge detection mapping process is performed to identify one or more maximum gradient transition points for each vessel. If the identified transition points are sufficiently close in proximity, a boundary will be established for the respective candidate vessel. The interior of the candidate vessel will then be analyzed to ensure sufficient image homogeneity exists therein. If so, the vessel is confirmed and the identified boundary thereof is highlighted or otherwise indicated. In the ultrasound image 262 of FIG. 14, the boundary of the automatically identified vessel 262A is indicated by highlighted perimeters 268.

In another embodiment, a clinician can locate and touch the display 30 to indicate the approximate center of a vessel imaged by the system 10. The system 10 can then execute the above edge detection mapping process and proceed from that point as described above.

The above examples of auto or user-assisted vessel/object detection can be used in one embodiment to provide further or more specific information to the user. For instance and as shown to the left of the ultrasound image 262 of FIG. 14, the particular depth and/or distance to the detected vessel 268 can be identified and depicted. Also and as shown in the gauge icon field 264 on the right side of the ultrasound image 262, the percentage amount of vessel occupation ("VO") for the detected vessel 268 can be displayed specific to the detected vessel. This further assists the user in choosing the properly-sized catheter/medical device to insert. These features can be employed on the embodiments described further above as well. For instance, in the embodiment described in connection with FIGS. 3-11, depiction of the in-vessel catheter length field 108 could be limited to the in-vessel catheter length corresponding to a vessel (here, the vessel 102A) that is automatically or semi-automatically identified in a manner similar to that described in connection with FIG. 14.

It should be remembered that the ultrasound system disclosed herein is but one example of a system in which the present embodiments can be practiced; other devices and systems that produce and/or depict ultrasound images can also benefit from the principles described herein.

Embodiments described herein may comprise a special purpose or general-purpose computer including computer hardware, as discussed in greater detail below. Embodiments within the scope of the present disclosure also include computer-readable media for carrying or having computer-executable instructions or data structures stored thereon. Such computer-readable media can be any available media that can be accessed by a general purpose or special purpose computer. By way of example, and not limitation, computer-readable media can comprise physical (or recordable-type) computer-readable storage media, such as, RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined herein as one or more data links that enable the transport of electronic data between computer systems and/or modules. When information is transferred or provided over a network or another communications connection (either hardwired, wireless, or a combination of hardwired or wireless) to a computer, the computer properly views the connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments herein may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones and devices, PDAs, pagers, and the like. The embodiments may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound imaging system for assisting with placement of a medical device near a target location within a blood vessel in a body of a patient, the system comprising:
   a console;
   a probe that remains external to the body and produces an ultrasound image of the target location;
   a processor;
   a memory including instructions capable of causing the processor, prior to insertion of the medical device into the body, to process data to determine a depth of the target location in the body, and to process data, including the depth of the target location, to determine a length of the medical device that will be disposed within the blood vessel when the medical device is inserted into the body; and
   a display for depicting the ultrasound image and the length of the medical device that will be disposed within the blood vessel.

2. The system as defined in claim 1, wherein the probe includes a needle guide, wherein the medical device includes an elongate device, and wherein the display further depicts depth information of the target location.

3. The system as defined in claim 2, wherein the elongate device includes a catheter including an overall length, wherein the length of the catheter that will be disposed within the blood vessel is less than the overall length.

4. The system as defined in claim 3, wherein a user can select different overall catheter lengths, and wherein the instructions are capable of causing the system to process data to determine the length of the catheter that will be disposed within the blood vessel for each of the selected overall catheter lengths.

5. The system as defined in claim 4, wherein, for each overall catheter length of the different overall catheter lengths, the display depicts the length of the catheter that will be disposed within the blood vessel at each of a plurality of depths indicated for the ultrasound image.

6. The system as defined in claim 5, wherein the display includes a touchscreen display, and wherein the display includes a button that enables toggling between each of the selected overall catheter lengths.

7. The system as defined in claim 6, wherein the processor can access a storage location including a lookup table, the lookup table including an in-vessel catheter length for each of the plurality of depths of the ultrasound image.

8. The system as defined in claim 1, further comprising a storage location where a lookup table is located, the lookup table including the length of the catheter that will be disposed within the blood vessel for at least one medical device.

9. The system as defined in claim 1, wherein the medical device includes at least one of a catheter, an access needle, and an infusion needle.

10. The system as defined in claim 1, wherein the ultrasound image is scalable in size and wherein the display includes a medical device size icon field that depicts various predetermined sizes of the medical device, the medical device size icon field being scalable so as to maintain a 1:1 ratio with the ultrasound image.

11. A method for conveying information from an ultrasound imaging system relating to insertion of a medical device into a patient body, the method comprising:
depicting an ultrasonic image of at least one target location within the patient body on a display, the ultrasonic image obtained from a probe that remains external to the patient body;
causing a processor of the ultrasound imaging system, prior to insertion of the medical device into the patient body, to process data to determine a depth of the at least one target location in the patient body, and to process data, including the depth of the at least one target location, to determine an internal length of the medical device that will be disposed within the patient body after the at least one target location when the medical device is inserted into the patient body; and
displaying the depth of the at least one target location and the internal length of the medical device on the display with the ultrasonic image, the depth of the at least one target location correlated with the ultrasonic image.

12. The method for conveying as defined in claim 11, wherein the medical device is an elongate medical device a portion of which is to reside within a vessel and wherein the internal length includes vessel depth-dependent information relating to how much of the elongate medical device is to reside within the vessel.

13. The method for conveying as defined in claim 12, wherein the elongate medical device is a catheter, and wherein the method further comprises determining the internal length for at least two catheters of differing overall lengths, the internal length differing for each of the at least two catheters.

14. The method for conveying as defined in claim 13, further comprising identifying the differing overall lengths of the at least two catheters via user input to the ultrasound imaging system.

15. The method for conveying as defined in claim 14, wherein depicting the ultrasonic image of the at least one target further comprises:
automatically defining the vessel via an edge detection and convolution algorithm; and
visually highlighting the vessel on the depicted ultrasonic image.

16. The method for conveying as defined in claim 14, wherein depicting the ultrasonic image of the at least one target further comprises:
receiving user input to identify a central portion of the vessel; and
executing a convolution algorithm to define a boundary of the vessel.

17. The method for conveying as defined in claim 11, wherein determining the internal length further comprises:
accessing a lookup table disposed in a memory location to acquire the internal length, the internal length based on an assumed angled insertion path from a needle guide disposed on an ultrasound probe of the ultrasound imaging system.

18. The method for conveying as defined in claim 11, wherein determining the internal length further comprises aligning the internal length to depth information on the depiction of the ultrasonic image.

19. A non-transitory, computer-readable medium including computer executable code that, when executed, causes a processor to process data to perform the following in relation to insertion of a medical device into a patient body:
depict on a display of an ultrasound imaging system an ultrasonic image of at least one target location within the patient body, the ultrasonic image obtained from a probe that remains external to the patient body;
determine, prior to insertion of the medical device into the patient body, a depth of the at least one target location in the patient body;
determine an internal length of the medical device that will be disposed within the patient body after the at least one target location when the medical device is inserted into the patient body; and
display the depth of the at least one target location and the internal length of the medical device on the display with the ultrasonic image, the depth of the at least one target location correlated with the ultrasonic image.

20. The computer-readable medium as defined in claim 19, further including executable code to automatically execute an edge detection algorithm to detect a circular vessel in the ultrasonic image.

21. The computer-readable medium as defined in claim 20, further including executable code to perform the following:
calculate a depth of the detected vessel, and
determine the proximity information relating to anticipated proximity of the medical device to the detected vessel at the calculated depth prior to insertion of the medical device into the body.

22. The computer-readable medium as defined in claim 19, further including executable code to perform the following:

receive user input to indicate a central portion of a vessel present in the ultrasonic image; and execute a vessel boundary detection algorithm to determine the boundary of the vessel present in the ultrasonic image.

23. A method of using an ultrasound imaging system in inserting a catheter into a vessel of a patient, the method comprising:

inputting into the ultrasound imaging system an overall length of the catheter to be inserted into the vessel;

ultrasonically imaging for depiction on a display the vessel with a probe of the ultrasound imaging device, the probe remaining external to the patient;

observing information provided by the ultrasound imaging system prior to catheter insertion, the information including an insertion length of a distal portion of the catheter that would be entirely disposed within the vessel after catheter insertion; and inserting the catheter into the vessel such that the insertion length of the distal portion is entirely disposed within the vessel.

24. The method of using as defined in claim 23, wherein the information provided by the ultrasound imaging system is provided according to one or more depths indicated on the ultrasound image.

25. The method of using as defined in claim 23, further comprising inputting a type of procedure for which the catheter is to be employed.

26. The method of using as defined in claim 23, wherein inputting the overall length of the catheter further comprises selecting one or more possible catheter lengths from a list of available lengths presented by the ultrasound imaging system.

27. The method of using as defined in claim 23, further comprising observing possible catheter gauges on the display to determine a desired gauge size for the imaged vessel.

28. The method of using as defined in claim 23, further comprising:

inputting into the ultrasound imaging system the overall length of an alternate catheter to be inserted into the vessel; and observing information provided by the ultrasound imaging system prior to alternate catheter insertion, the information relating to the length of a distal portion of the alternate catheter that would be disposed within the vessel after alternate catheter insertion.

29. The method of using as defined in claim 23, wherein ultrasonically imaging further comprises identifying a depth of the vessel, and wherein observing information further comprises observing information provided by the ultrasound imaging system prior to catheter insertion.

30. The method for conveying as defined in claim 11, wherein the target location is a reservoir of an access port previously implanted within the body, wherein the medical device is an access needle for delivering fluids to the access port, and wherein the proximity information relates to the depth to which one or more needles of predetermined overall lengths will descend in relation to the depth of the access port.

* * * * *